United States Patent
Hahn et al.

[11] Patent Number: 5,720,870
[45] Date of Patent: Feb. 24, 1998

[54] DETERMINING GAS CONCENTRATION

[75] Inventors: Clive Hahn, Radley; David Clark, Tyne and Wear, both of United Kingdom

[73] Assignee: ISIS Innovation Limited, Oxford, United Kingdom

[21] Appl. No.: 564,215

[22] PCT Filed: Jun. 17, 1994

[86] PCT No.: PCT/GB94/01308

§ 371 Date: Jan. 5, 1996

§ 102(e) Date: Jan. 5, 1996

[87] PCT Pub. No.: WO95/00838

PCT Pub. Date: Jan. 5, 1995

[30] Foreign Application Priority Data

Jun. 18, 1993 [GB] United Kingdom ............... 9312578

[51] Int. Cl.⁶ ........................................ G01N 27/404
[52] U.S. Cl. ........................ 205/783; 204/415; 205/781
[58] Field of Search ........................... 204/415, 434; 205/782, 782.5, 783, 780.5, 781, 785.5, 787

[56] References Cited

U.S. PATENT DOCUMENTS 4,062,750  12/1977  Butler ........................... 204/415
4,148,305   4/1979  Reichenberger ............... 204/415
4,851,088   7/1989  Chandrasekhar et al. ....... 204/415

FOREIGN PATENT DOCUMENTS 0027005   4/1981  European Pat. Off.
0162622  11/1985  European Pat. Off.
0239296   9/1987  European Pat. Off.
0329322   8/1989  European Pat. Off.
2158250  11/1985  United Kingdom.

OTHER PUBLICATIONS

Compton et al, "Novel Amperometric Sensor for the Detection of the Anaesthetic Gases Isoflurane and Nitrous Oxide", *J. Chem. Soc. Faraday Trans.*, 1990 Month Unavailable, 86(7), pp. 1077–1081.

*Primary Examiner*—T. Tung
*Attorney, Agent, or Firm*—Nixon & Vanderhye P.C.

[57] ABSTRACT

Method and device for determining the concentration of one or more gases, e.g. $O_2$ or $CO_2$ or an anaesthetic gas, in a fluid e.g. a body fluid or a gas mixture. A membrane (12) permeable to the gases retains a solvent (22) e.g. dimethylsulphoxide. In contact with the solvent is a working electrode (24) of a surface area preferably less than 10 μm². The potential of the working electrode is sept, over a range to reduce each of the one or more gases, and at a rate to minimize cross-reactions between gases and their reduction products.

9 Claims, 12 Drawing Sheets

O₂ SUBTRACTED. SR = 0.5v/s

10% O₂  3, 5.7, 8.5% CO₂

DETERMINING GAS CONCENTRATION

BACKGROUND OF THE INVENTION

1. Field of the Invention

This invention relates to a method and device for determining the concentrations of one or more gases in a fluid. The fluid may be in the liquid or gas phase and is, for example, a body fluid such as serum. The invention is of primary interest for determining the concentrations of oxygen and carbon dioxide, as well as nitrous oxide and certain anaesthetic gases. But the principles of the invention are applicable to other gases.

2. Discussion of Prior Art

The continuous measurement of $O_2$ and $CO_2$ in clinical medicine has led to a whole industry of measurement devices. In the blood, oxygen is measured by the amperometric Clark $PO_2$ electrode; and $CO_2$ is measured by the potentiometric (glass electrode) Stow-Severinghaus electrode. Thus two sensors, working on entirely different principles, have to be employed whenever $PO_2$ and $PCO_2$ are measured. Blood-gas analyzers therefore use two separate sensors. Intravascular measurements can only be made for $PO_2$, using Clark cells fabricated on the tip of a polymer catheter. It has proved impossible, so far, to miniaturize the glass electrode, and so measure intravascular $PCO_2$, with the Stow-Severinghaus technique. Paediatric intravascular oxygen sensors have been successfully developed, first by D. G. Searle and then by Hoffman la Roche, for paediatric use, and these sensors are now manufactured by Biomedical Sensors Ltd. (High Wycombe).

In the gaseous phase, oxygen is measured with Clark-type sensors for steady-state analysis (e.g. for anaesthetic machines); and by fast paramagnetic analyzers for breath-by-breath analysis. Expired $CO_2$ is almost inevitably measured with an infrared analyzer.

Outside medicine, as the control of $CO_2$ increases in importance in various technologies, there is an ever growing need for inexpensive $CO_2$ sensors with high sensitivity and selectivity. Such examples include the fermentation industry in general; brewing; on-line industrial monitoring; pollution measurement; $CO_2$ level measurement in large auditoria; vehicle exhaust analysis, etc. In many instances it would be a great advantage to be able to measure $O_2$ simultaneously, with the same sensor measuring both $O_2$ and $CO_2$, and using the same analysis principle.

At potentials of the order of $-0.5$ to $-1.0$ V, against Ag/AgCl reference electrode, in an aprotic solvent such as DMSO, oxygen in solution is reduced by the reaction:

$$O_2 + e \rightarrow O_2^-  \quad (1)$$

This superoxide radical is stable for short periods in non-aqueous solvents. But it reacts rapidly with carbon dioxide, by a series of reactions which may be summarised as:

$$2O_2^- + 2CO_2 \rightarrow C_2O_6^{2-} \quad (2)$$

At potentials in the range $-1.5$ to $-2.5$ V, dissolved carbon dioxide is reduced, initially by virtue of the reaction:

$$CO_2 + e \rightarrow CO_2^- \quad (3)$$

European patent 162622 describes a gas sensor and method which used reactions (1) and (2) to provide a simultaneous determination of oxygen and carbon dioxide concentrations. There was described a pulsed $CO_2$ titration technique, whereby the electrode surface was kept deliberately large in order to produce enough $O_2^-$ to consume all the $CO_2$ present. A pulsed voltage sufficiently negative to reduce the $O_2$ molecule (but not sufficiently negative to reduce $CO_2$) was first applied to the electrode surface, followed by an oxidizing pulse to oxidize those $O_2^-$ ions which had remained after reacting with the $CO_2$ molecules.

The problems with this technique were that a large cathode surface was needed, leading to high sample consumption; a complicated mathematical relationship was required to extract the $CO_2$ concentration, and the measured $O_2$ concentration was complicated by the enhancement of its signal from the chemical reactions (1) and (2) shown above.

SUMMARY OF THE INVENTION

It is an object of this invention to provide a device and method by which these problems may be overcome. This is achieved by using reactions (1) and (3) above under conditions to minimize interference from reaction (2).

Apart from oxygen and carbon dioxide, there is also a need for improved techniques for determining the concentrations of other gases such as nitrous oxide ($N_2O$) and gases used in anaesthesia. Devices for the clinical measurement of $N_2O$ and the anaesthetic gas halothane, based on amperometric electrochemical sensing, are known. For example, $N_2O$ and halothane may be measured on silver cathodes in aqueous electrolytes (Clin. Phys. Physiol. Meas., 8 (1987) 3-38). However, isoflurane, the popular anaesthetic gas, has heretofore been considered to be electrochemically inert over a wide range of electrode materials in both aqueous and non-aqueous solution (J. Electroanal. Chem. 244(1988) 203-219) and thus unsuited to such techniques.

In particular, there is a need for equipment that is capable of accurately measuring the concentrations of a range of gases, either separately or as components in a mixture of gases, and which is easy to use and relatively inexpensive. The present invention seeks to provide such apparatus and a method for its use.

In one aspect the present invention provides a device for determining the concentrations of one or more gases in a fluid, comprising a membrane permeable to the gas or gases, a solvent for the gas or gases and which is retained by the membrane, a working electrode having a surface area less than 10000 square microns in contact with the solvent, a counter and/or reference electrode in contact with the solvent, means for applying to the working electrode a potential and for sweeping the potential over a range effective to reduce the gas or gases in the solvent and at a rate sufficient to minimize the interfering effect of any reaction between one gas and a reduction product of any other, and means for measuring the current generated at a predetermined potential as indication of the concentration of the first gas, and where the concentrations of two or more gases are being determined, means for measuring the current generated at each of one or more further predetermined potentials as an indication of the respective concentrations of the one or more other gases present.

In another aspect the invention provides a method of determining the concentrations of one or more gases in a fluid, which method comprises applying the fluid to one side of a membrane permeable to the gas or gases, the other side of the membrane retaining a solvent for the gas or gases, using a working electrode having a surface area less than 10000 square microns in contact with the solvent to apply a potential which is swept over a range effective to reduce the gas or gases in the solvent, wherein the rate of sweep of potential is sufficient to minimize the interfering effect of any reaction between one gas and a reduction product of any other, measuring the current generated at a predetermined potential as an indication of the concentration of the first gas, and, where the concentrations of two or more gases are being determined, measuring the current generated at each of one or more further predetermined potentials as an indication of the respective concentrations of the one or more other gases present.

The device and method may be used to determine the concentration of a single gas or of two, three or more gases simultaneously. In addition to gases such as $O_2$, $CO_2$ and $N_2O$, it has been found that the concentrations of anaesthetic gases such as the following can also be determined by this means:

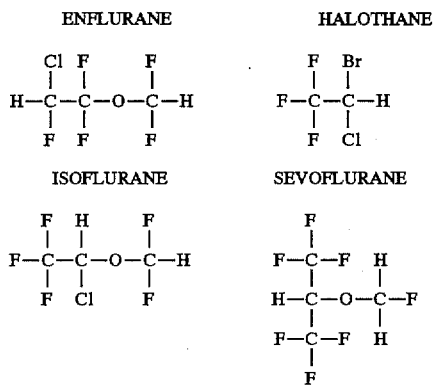

This finding is considered to be particularly surprising since, as noted above, isoflurane has previously been regarded as electrochemically inert. However, we have now shown that such gases can be reduced using a working electrode of the aforementioned size and a suitable solvent.

The fluid may be a gas or a liquid, e.g. a body fluid such as serum. The membrane is selected according to the nature of the gas or gases under investigation. For $O_2$, $CO_2$ and/or $N_2O$ gases, for example, the membrane may suitably be of a material such as PTFE. In the case of volatile anaesthetic gases, however, the membrane would preferably be of an inert porous material (such as sintered glass) which would not be attacked by the solvent. The solvent may be dimethylsulphoxide (DMSO), although other non aqueous solvents including acetonitrile and propylene carbonate are possible. The solvent may contain a small amount of a scavenger, for example for the superoxide ion, such as water. Though not preferred, it is possible and may be convenient to use a solvent containing a minor proportion of water, e.g. up to 10% v/v or even higher. A conductivity improver such as TEAP may also be present. The working electrode may be of silver or carbon or platinum or more preferably of gold and the counter electrode may be of platinum. A reference electrode, e.g. of Ag/AgCl, may be included in the system.

The potential of the working electrode is swept over a range which is effective to reduce each of the gases in the solvent. The range to be covered is therefore dependent upon which gas or gases are involved in any given instance, but would typically be from −0.5 V to −2.5 V or greater (i.e. more negative). For oxygen and carbon dioxide, for example, the range is (as noted above) approximately −0.5 V to −2.5 V, though the reduction potentials of the two gases do depend on various other factors. This sweeping is performed under conditions which minimize the interfering effect of any reaction between one gas (carbon dioxide) and a reduction product of the other (superoxide ion). In other words, the system is operated under conditions to minimize reaction (2) above. This reaction is considered to be minimized if its extent is so small as not substantially to affect the measurements of oxygen and carbon dioxide concentration recorded. Three major factors are involved here, and each will be discussed in turn:

The size of the working electrode;
The rate of potential sweep;
Other characteristics of the potential sweep profile.

The working electrode is specified as having a surface area below 10000 square microns (i.e. 100 μm)$^2$; above this figure it is difficult or impossible to avoid increasingly significant interference due to reaction (2) above. The working electrode surface area is preferably below 1000 square microns, since above this value a rather high rate of potential sweep may be necessary in order to avoid interfering reactions.

The working electrode Surface area is preferably no more than 100 square microns (i.e. 10 μm)$^2$; as shown below, good results can be obtained under these circumstances without any limitation on the rate of potential sweep. More preferably, the working electrode surface area is less than 10 square microns; as shown below, such electrodes can give more accurate results with less correction required to compensate for interfering reactions.

It is expected that working electrodes with surface area below 1 square micron will have added advantages. A sheet of insulating material may carry an array of such electrodes, for example in pores extending through the sheet. The total current will be the product of each individual cathode current and a number of cathodes, and redundancy will be built in if some cathodes fail. Microelectrodes will reduce gas/liquid difference effects, and will allow thin membranes to be used, thus decreasing the time response of the sensor. Microelectrodes will need to be spaced apart, e.g. at least 5 and preferably at least 20 cathode radii, from each other so as to avoid cross-talk effects between adjacent electrodes. There is in principle no lower limit on the size of a microelectrode.

The rate of potential sweep is another important factor. If the rate is too fast, it is found that the results obtained are not accurate or reproducible. With existing equipment, a preferred maximum rate of sweep is 50 V/s although higher rates may be possible with more sophisticated equipment. As the rate of potential sweep is slowed, two problems eventually arise. The first is simply that the information (required to determine gas concentrations) takes longer to obtain. In cases where speed of response is important, a rate of sweep of at least 0.01 V/s, e.g. 0.1 to 10 V/s, is likely to be preferred.

The other problem is that, in the case of a mixture of $O_2$ and $CO_2$ gases, if the rate of potential sweep is too slow, interference may arise from the unwanted reaction (2) above between carbon dioxide and superoxide ion. Our work has shown that, provided the surface area of the (or each) working electrode is no more than 100 square microns, this problem does not arise in practice. Under these circumstances, the optimum rate of potential sweep is one which generates accurate information as quickly as possible, and is likely to be in the range of 0.1 to 10 V/s. With working electrodes with larger surface area, other rates of sweep may be appropriate.

Other characteristics of the potential sweep profile are subject to many variations. In a simple case, for example, the potential of the working electrodes starts at −0.5 V, is raised to −2.5 V at a rate of 0.5 V/s, is reduced to −0.5 V at a rate of 0.5 V/s, and is immediately again raised to −2.5 V at the same rate and so on. The two end figures, of −0.5 V and −2.5 V, can be varied, provided only that the potential range covers the reduction potentials of the two gases concerned. The rate at which the potential is changed from −2.5 V to −0.5 V can be higher, e.g. infinite. The rates of sweep do not have to be linear, there may be pauses, at either end or intermediate the ends of the range.

Improved results may be obtained if the working electrode is pre-conditioned immediately before measurement is started. For example, the working electrode may be pre-conditioned at some potential within the sweep range, e.g. −1.0 V or −1.9 V for a short period, e.g. 1 to 60 s, prior to measurement.

The device and method of this invention enable the concentrations of a number of gases to be determined, using the same electrode and solvent, by sweeping the appropriate voltage range. They are suitable not only for the determination of blood-gas concentrations, but for a variety of other gases as well. It is envisaged that apparatus based on this approach could also be used for more general vapour analysis and as a volatile agent monitor. Applications would include the medical field, for example on anaesthetic machines, and in the food industry.

BRIEF DESCRIPTION OF THE FIGURES

Reference is directed to the accompanying drawings in which:

FIGS. 20 to 23 are further graphs of current against voltage for various anaesthetic gases obtained using the alternative working electrode in the bench reaction cell.

DETAILED DISCUSSION OF PREFERRED EMBODIMENTS

Figure 1:
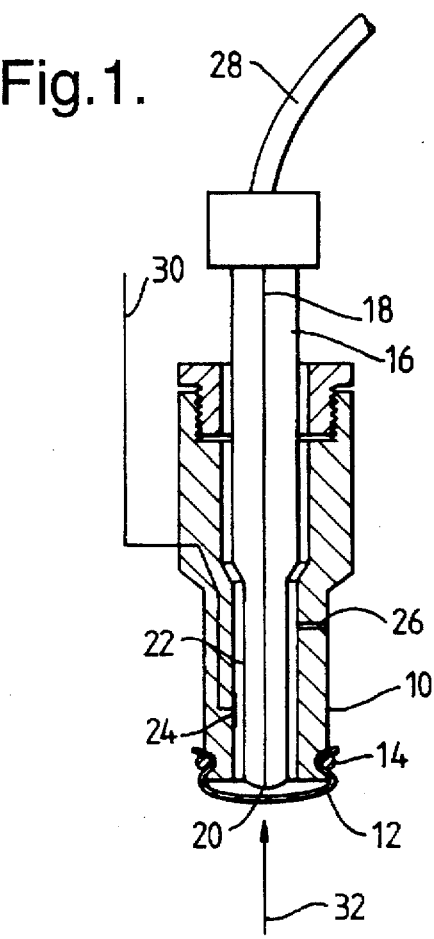
FIG. 1 is a schematic diagram of a sensor according to the invention.

The sensor shown in FIG. 1 comprises a generally tubular PTFE body 10, one end of which is closed by means of a PTFE membrane 12 sealed to the body by an "O" ring 14.

A working electrode comprises a glass rod 16 Containing an axially extending 10 μm diameter gold wire 18, the exposed end 20 thereof constituting the working electrode. The glass rod is positioned in the PTFE body with the working electrode adjacent the inner surface of the PTFE membrane. A region 22 surrounding the glass rod and retained by the PTFE body 10 and membrane 12 is filled with dimethylsulphoxide. An Ag/AgCl reference electrode 24 or an Ag quasi-reference electrode is also in contact with the DMSO. A DMSO overspill hole 26 is provided in the PTFE body. Leads 28 and 30 connect the working electrode and the reference electrode respectively to a power source (not shown) and an ammeter (not shown).

In use, the sensor is presented to a gas stream 32, for example containing oxygen and carbon dioxide, portions of which pass through the PTFE membrane 12 and become dissolved in the DMSO solvent 22. The potential of the working electrode 20 is scanned at a suitable rate cyclically between, say, −0.2 V and −2.3V, and the current flowing at particular potentials noted. For example, the current flowing at −0.8 V may be indicative of the oxygen concentration of the gas, while the current flowing at −1.9 V may be indicative of the carbon dioxide concentration in the gas. The optimum potential, or range of potentials, at which current is measured may depend to some extent on the particular characteristics of the apparatus. The total current flowing will be dependent, among other things, on the surface area of the working electrode. It will generally be necessary to compare the currents generated by an unknown gas stream with the currents generated by gas streams of known composition.

Figure 2:
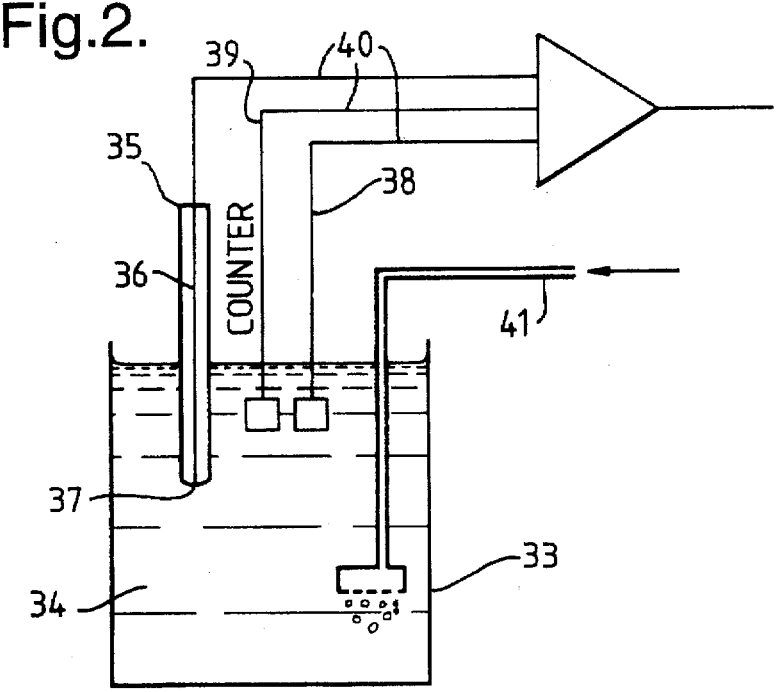
FIG. 2 is a schematic diagram of a bench reaction cell which includes a working electrode (but not behind a membrane).

The reaction cell shown in FIG. 2 comprises a glass body 33 containing a mixture of DMSO and TEAP as solvents 34. A working electrode comprises a glass rod 35 containing an axially extending gold wire 36, the exposed end 37 thereof constituting the working electrode. The glass rod is positioned in the glass body with the working electrode submerged in the DMSO/TEAP solution. An Ag/AgCl reference electrode 38 or an Ag quasi-reference electrode and a counter-electrode 39 are also in contact with the solvent mixture. The three electrodes are connected by leads 40 to a potentiostat (not shown).

In use, the gases/vapours under analysis are introduced into the reaction cell through an inlet pipe 41 and become dissolved in the DMSO/TEAP solvents. The cell volume is typically less than 1 ml so that the vapour/liquid equilibration time is reduced to a minimum. Working electrodes in which the gold wire had a diameter of either 2 μm or 10 μm were available for use. The potential of the working electrode is scanned at a suitable rate cyclically and the current flowing at particular potentials noted, as with the device of FIG. 1.

It will be appreciated that the reaction cell of FIG. 2 works on the same principle as the sensor of FIG. 1, except that in the latter the working electrode is behind a membrane. Thus, results obtained with the reaction cell would be expected to be reproduced when the same gas/vapour mixture is analysed using the sensor device according to this invention.

EXAMPLE 1

FIGS. 3 to 7 represent results obtained with the sensor shown in FIG. 1. The working electrode was a gold wire of 10 μm diameter. The membrane was of 12 μm PTFE. Measurements were made at room temperature, with the sensor inserted into a flowing gas stream of oxygen and carbon dioxide in nitrogen. Cyclic voltammograms were obtained at sweep rates of 0.5 V/s, with a pre-conditioning signal of −1.0 V for 10 s prior to the voltage sweep.

Figure 3:
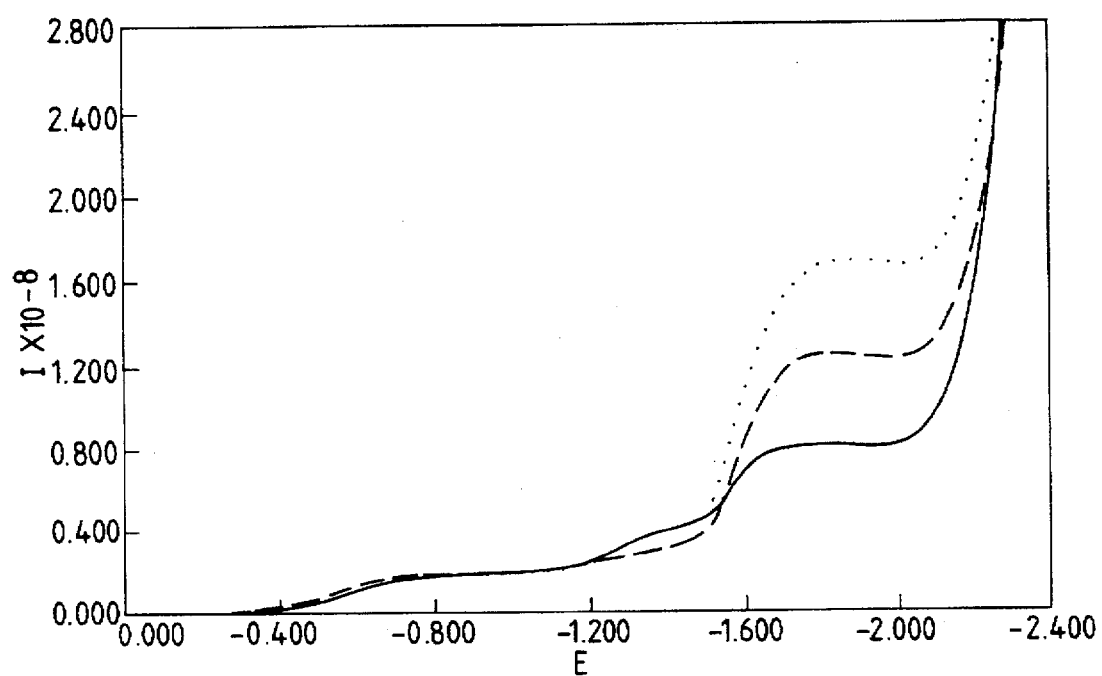
FIGS. 3 and 4 are graphs of current against voltage obtained using a particular working electrode.
Figure 4:
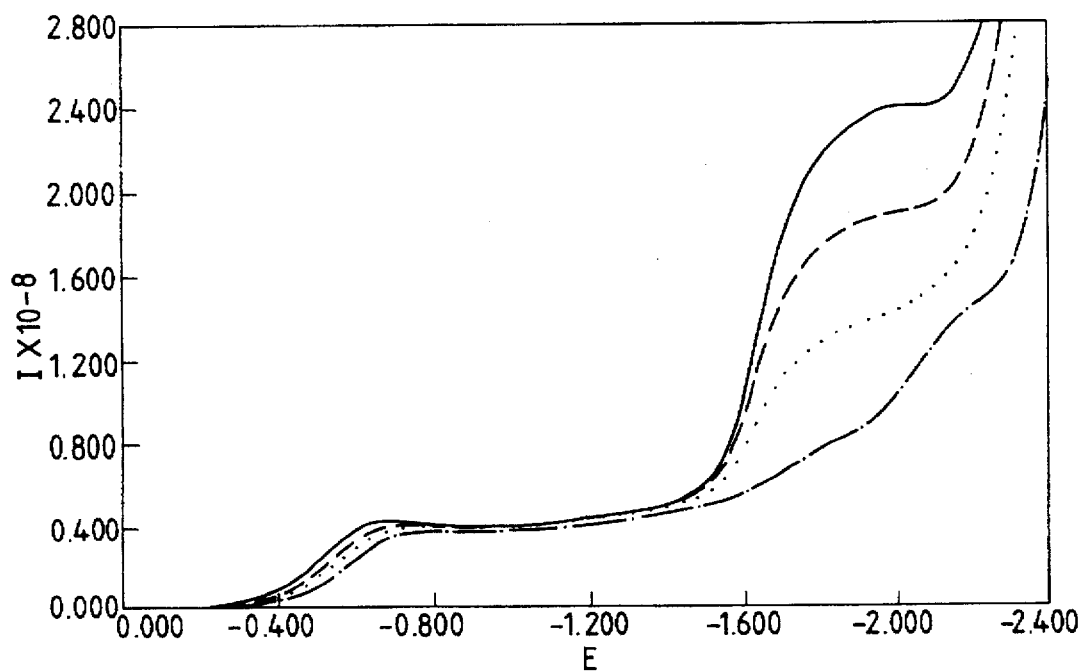

FIG. 3 is a voltammogram obtained at constant 10% v/v oxygen and 3, 6 and 9% carbon dioxide, balance nitrogen. FIG. 4 is the same type of voltammogram at constant 30% oxygen and 3, 6, 9 and 12% carbon dioxide. In both graphs, an oxygen current can be read at −0.8 V, with no evidence of any carbon dioxide feedback effect on the oxygen signal. A carbon dioxide current can be read at −1.9 V.

Figure 5:
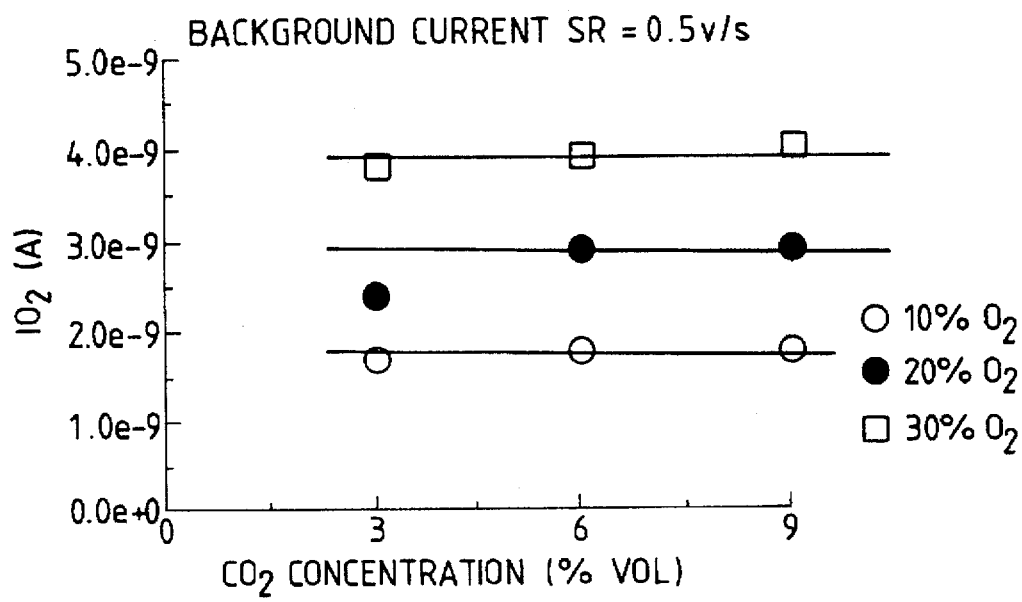
FIGS. 5, 6 and 7 are corresponding graphs of current against gas concentration obtained using the same working electrode.

FIG. 5 is a graph of oxygen current against carbon dioxide concentration, data having been taken from graphs such as FIGS. 3 and 4 at −0.8 V. It is apparent that the oxygen current is not significantly affected by the carbon dioxide content of the gas.

Figure 6:
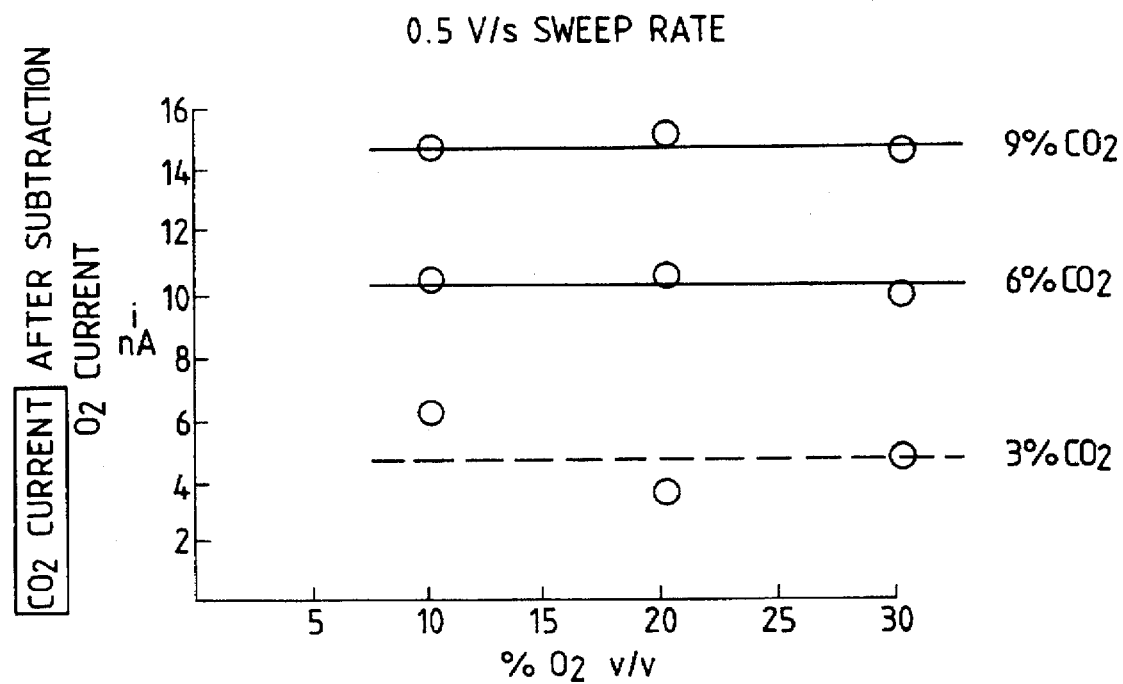
Figure 7:
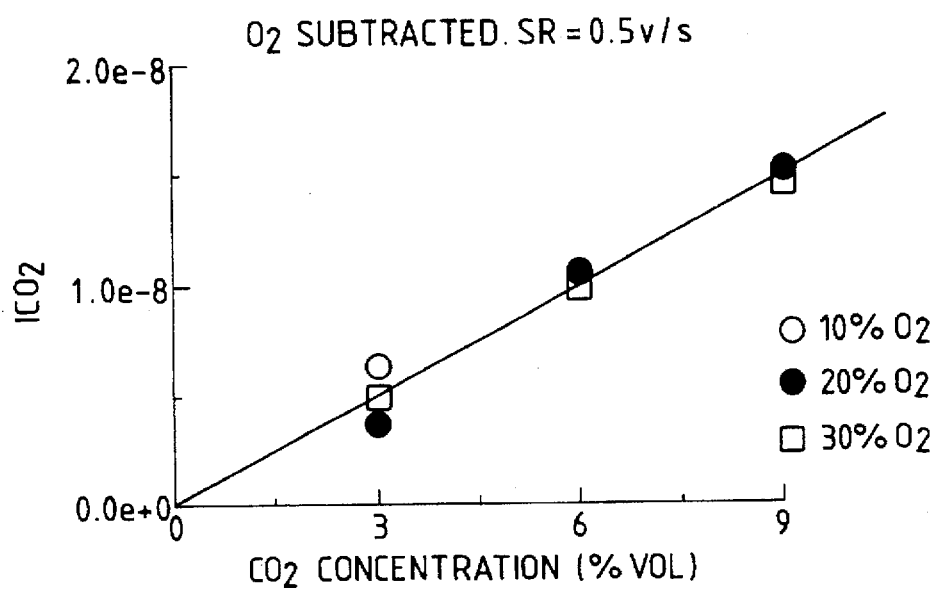

FIG. 6 is a graph of carbon dioxide current (after subtraction of the oxygen current) against oxygen content for three different levels of carbon dioxide concentration. Again, it is apparent that the carbon dioxide current is not significantly dependent upon oxygen concentration of the gas stream. The same data is replotted in FIG. 7 in the form of a graph of carbon dioxide current against carbon dioxide concentration. Apart from experimental scatter at 3% carbon dioxide, good linearity is demonstrated.

EXAMPLE 2

FIGS. 8 to 11 show results obtained in a rather different system. The electrode was constituted by the exposed end of a 2 μm diameter gold wire. The gas was dried and its temperature controlled at 37° C. Otherwise conditions were as for Example 1.

Figure 8:
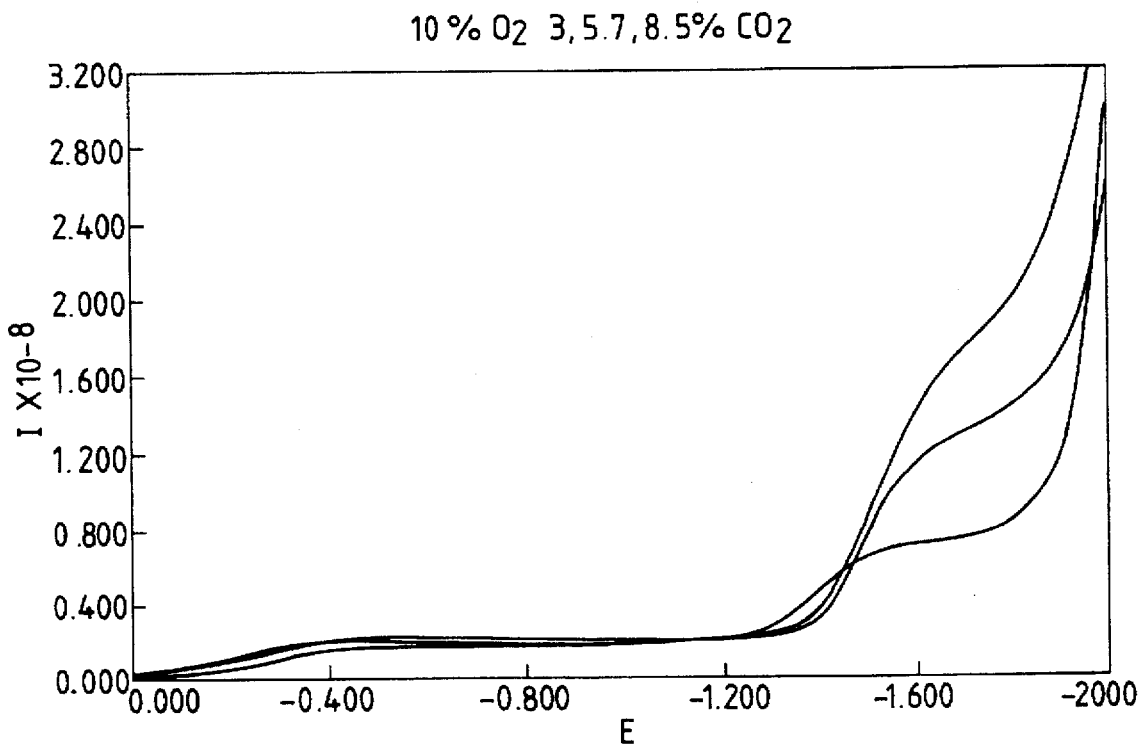
FIGS. 8 and 9 are graphs of current against voltage obtained using a second working electrode.
Figure 9:
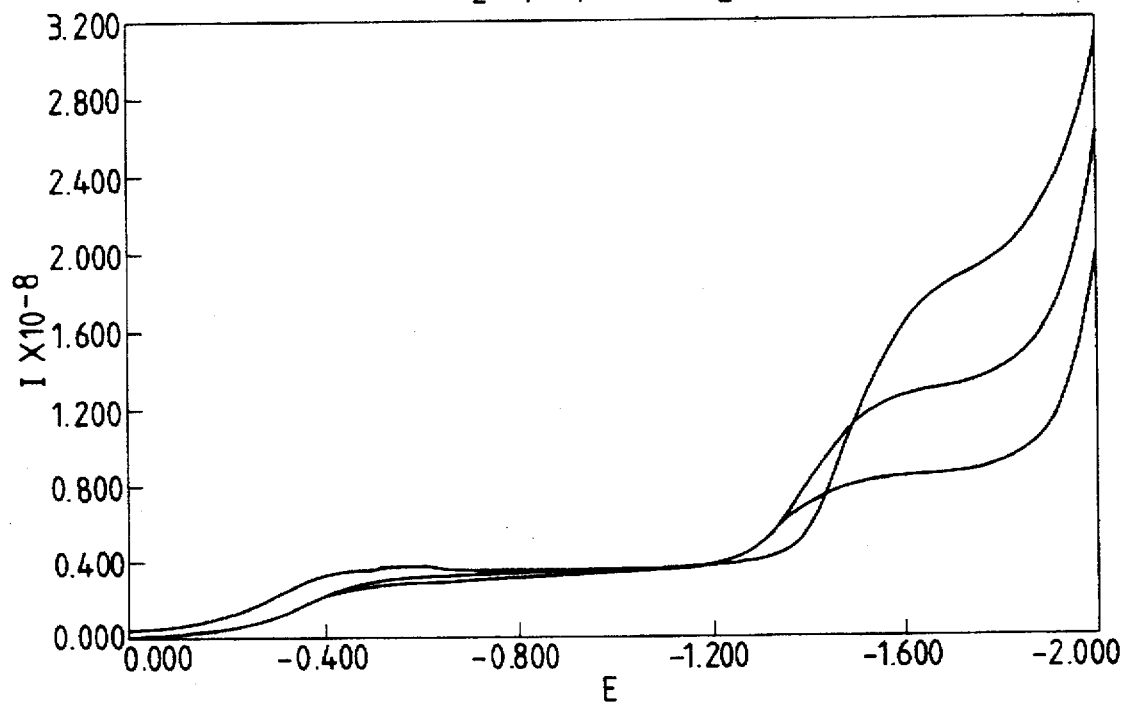

FIG. 8 is a graph of voltage against current for gas containing 10% v/v oxygen and 3, 5.7 and 8.5% carbon dioxide. FIG. 9 is a corresponding graph obtained using gas containing 20% oxygen.

Figure 10:
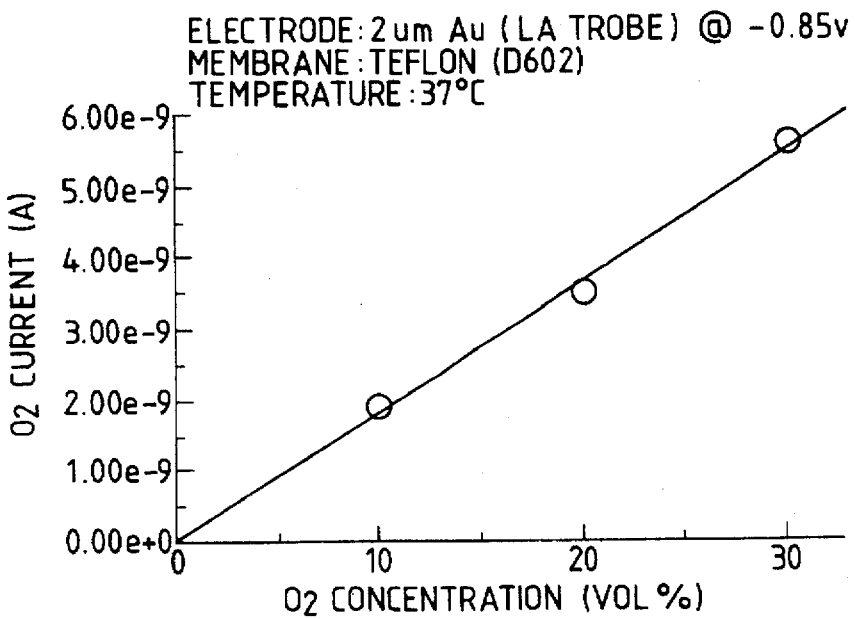
FIGS. 10 and 11 are graphs of current against gas concentration obtained using the second working electrode.

FIG. 10 is a graph (obtained from data such as that shown in FIGS. 8 and 9) of oxygen current against oxygen concentration, the current measurements having been made at −0.85 V. Good linearity is demonstrated.

Figure 11:
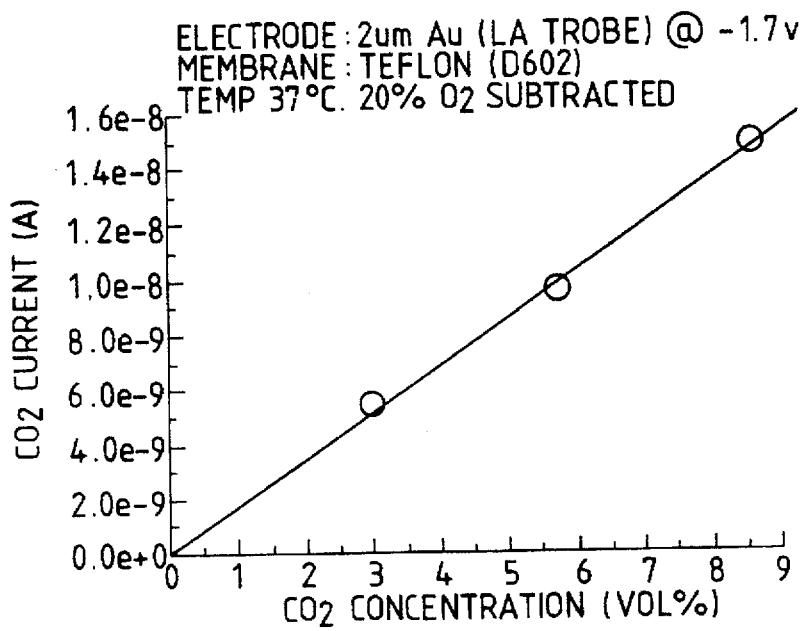

FIG. 11 is a graph (obtained from data in FIG. 9) of carbon dioxide current (with oxygen current subtracted) against carbon dioxide concentration. The measurements were made at −1.7 V potential. Again, good linearity is demonstrated.

EXAMPLE 3

FIGS. 12 to 15 illustrate the measurement of three gases at the same time and were obtained using the bench reaction cell shown in FIG. 2.

Figure 12:
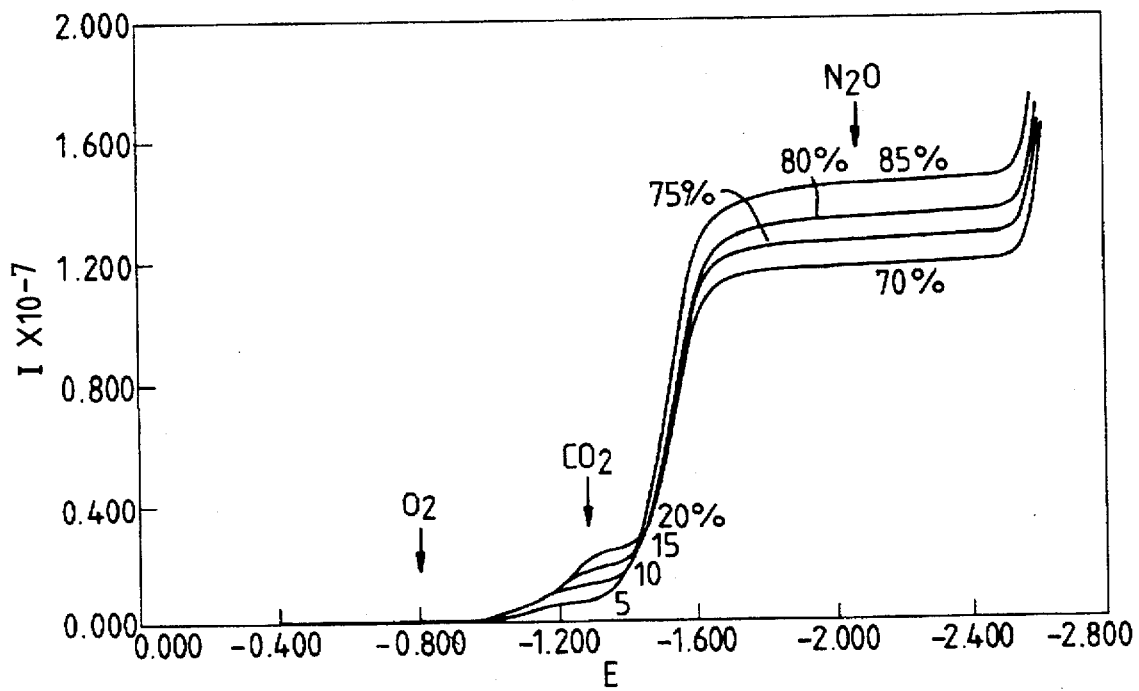
FIGS. 12, 13 and 14 are further graphs of current against voltage obtained using a working electrode in the bench reaction cell.
Figure 13:
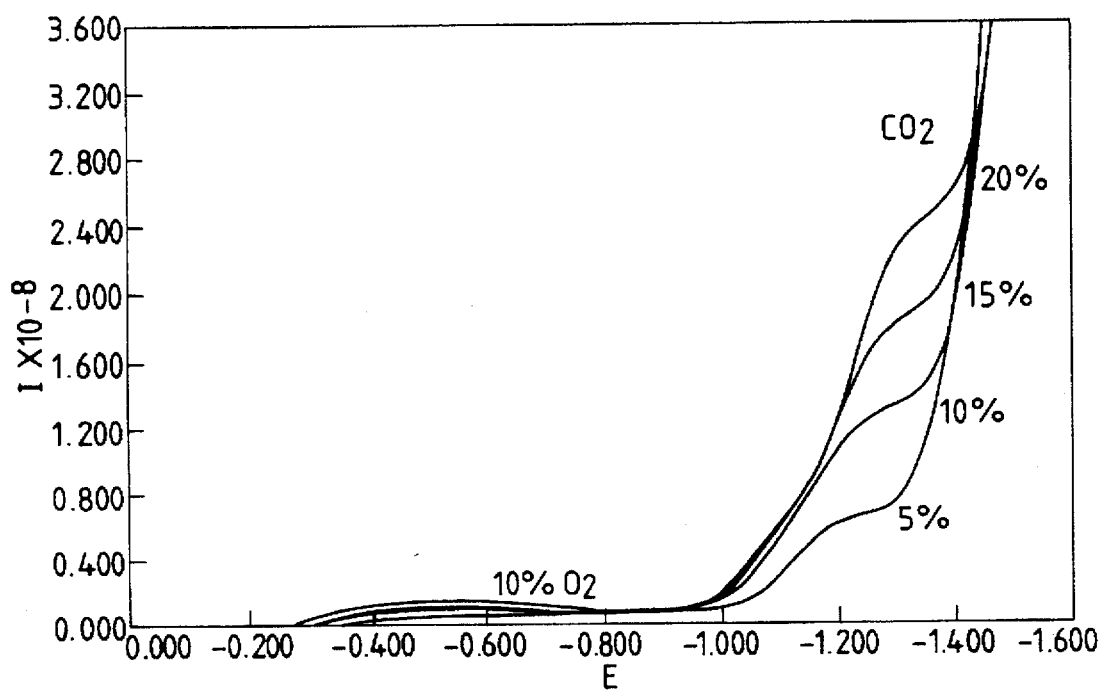
Figure 14:
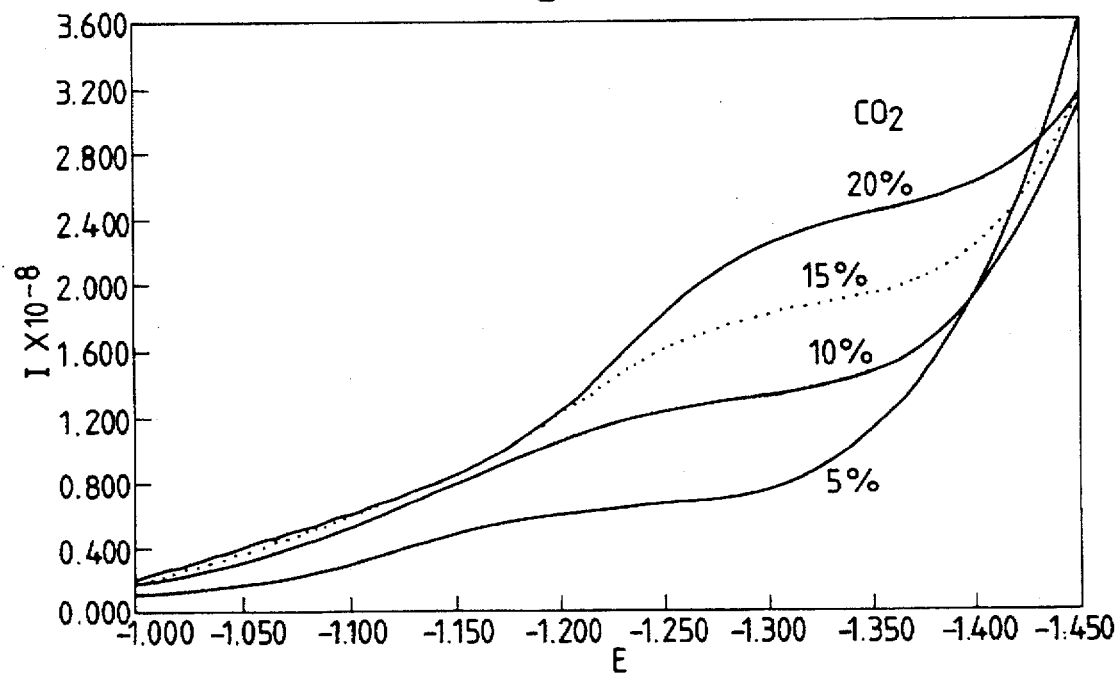
Figure 13:
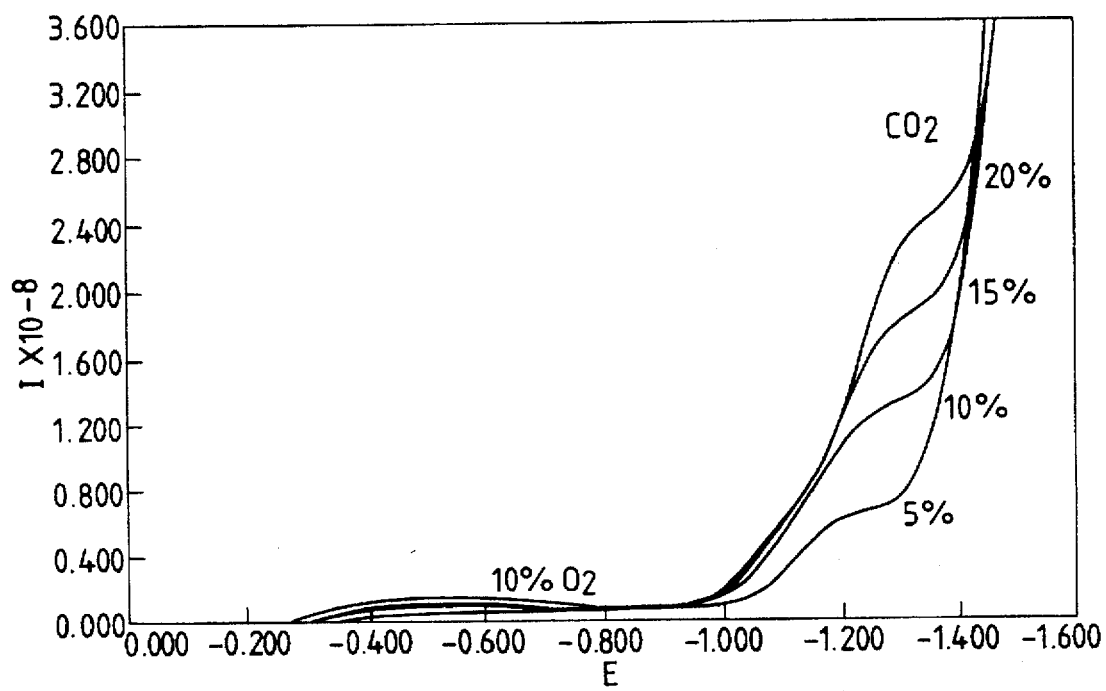
Figure 14:
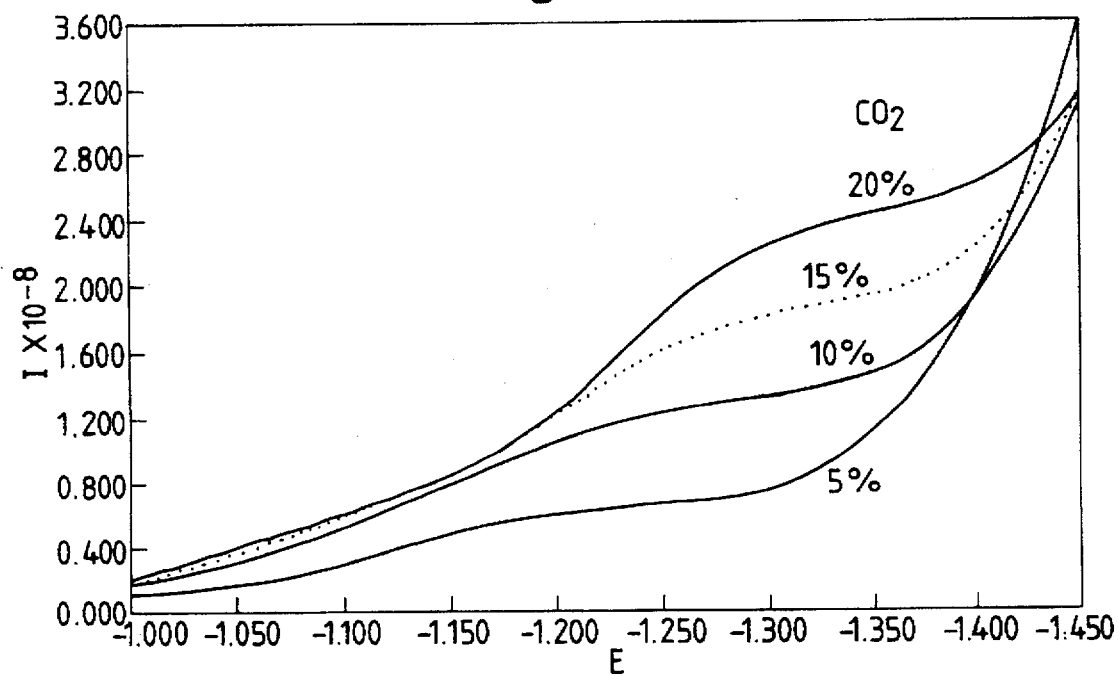
Figure 15:
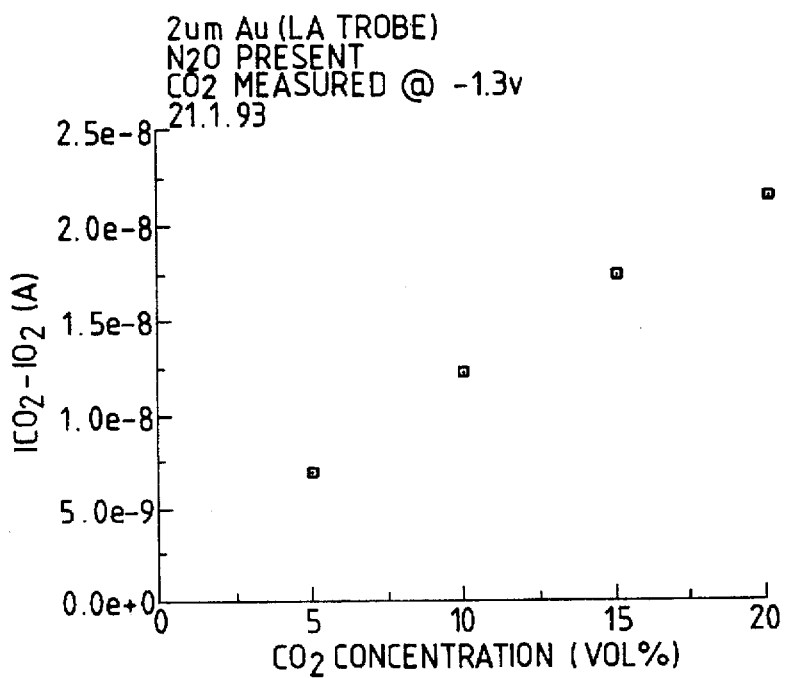
FIG. 15 is a graph of current against gas concentration ($CO_2$) obtained using a working electrode in the bench reaction cell.

FIG. 12 is a graph of voltage against current for a gas mixture containing 10% v/v oxygen and 5, 10, 15 and 20% carbon dioxide, with the balance being nitrous oxide. The oxygen signal is very low compared to the carbon dioxide and nitrous oxide signals, but is more clearly seen in FIG. 13 (which also magnifies the carbon dioxide current). In FIG. 14, both the voltage scale and the carbon dioxide current are magnified further. FIG. 15 is a graph of carbon dioxide current against carbon dioxide concentration, and shows that the carbon dioxide signal is linear with concentration. Other results (not presented) demonstrate that both the oxygen and nitrous oxide current are also linear with the respective concentrations of those gases.

EXAMPLE 4

FIGS. 16 to 19 illustrate the measurement of oxygen and nitrous oxide in the absence of carbon dioxide, and were obtained using the bench reaction cell shown in FIG. 2.

Figure 16:
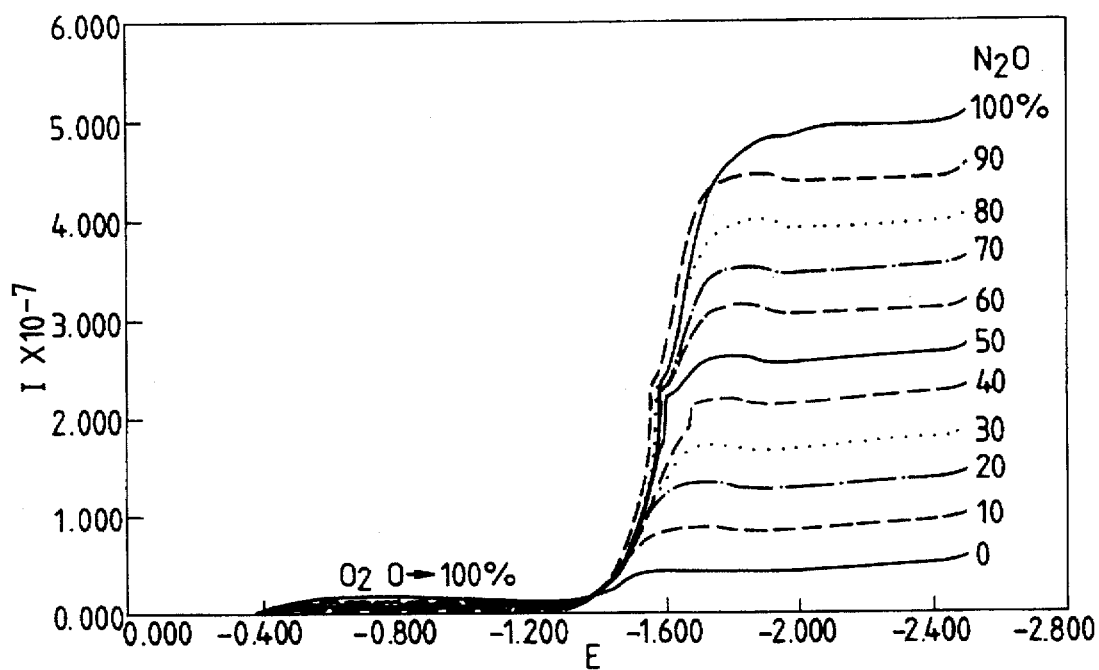
FIGS. 16 and 17 are further graphs of current against voltage obtained using an alternative working electrode in the bench reaction cell.
Figure 17:
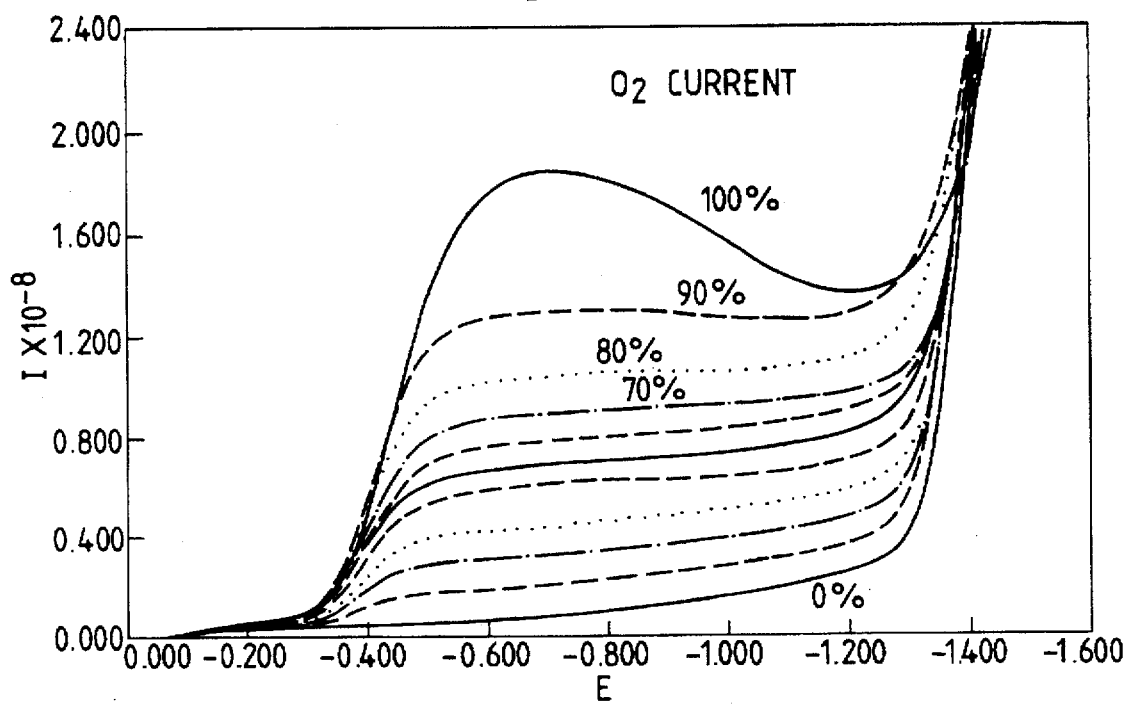

FIG. 16 is a graph of voltage against current for gas containing a mixture varying from 0 to 100% v/v·of oxygen and nitrous oxide. It will be seen that the nitrous oxide currents are massive compared to the oxygen currents. In FIG. 17, the oxygen current is magnified.

Figure 18:
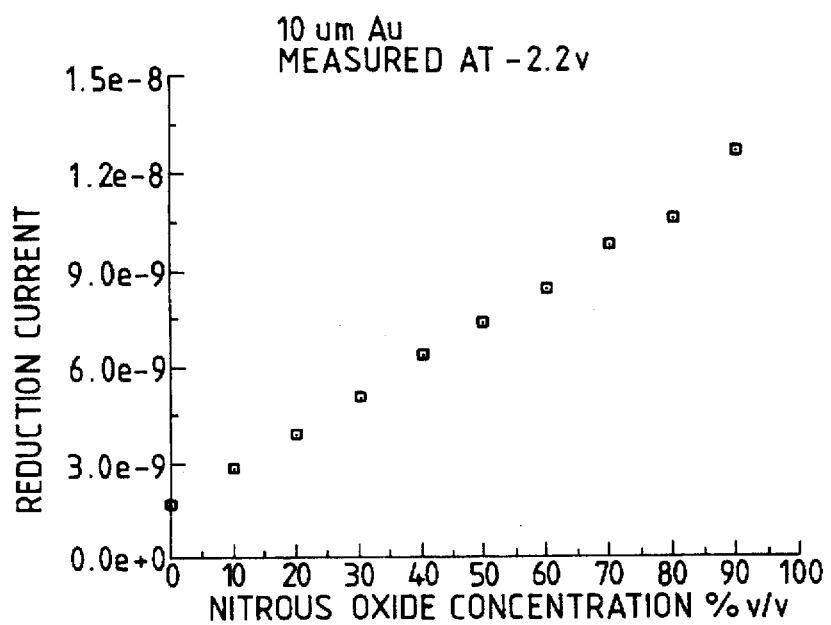
FIGS. 18 and 19 are graphs of current against gas concentration ($N_2O$ and $O_2$, respectively) obtained using the alternative working electrode in the bench reaction cell.
Figure 19:
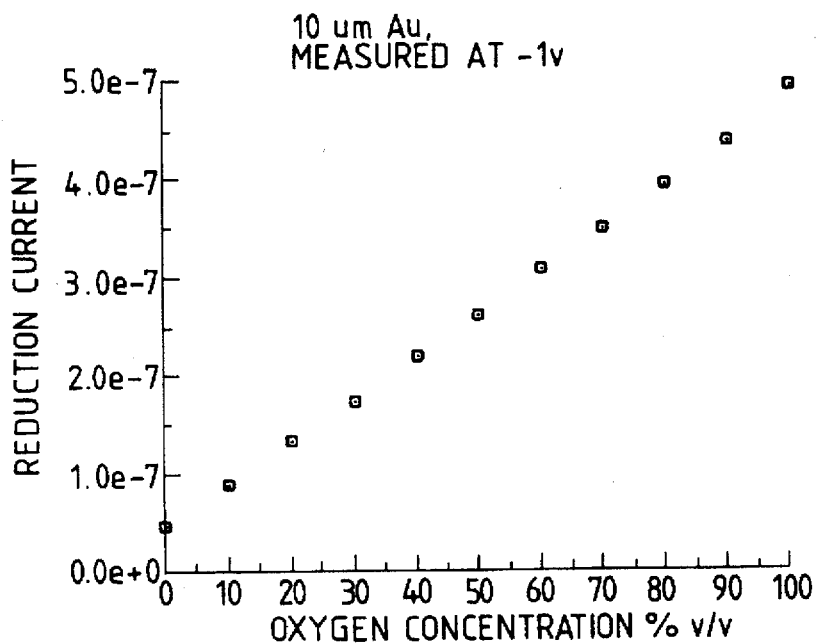

FIGS. 18 and 19 are graphs (obtained from data shown in FIGS. 16 and 17) of current against nitrous oxide concentration and oxygen concentration, respectively. Good linearity is demonstrated.

EXAMPLE 5

FIGS. 20 to 23 illustrate the determination of concentrations of four volatile agents, namely the anaesthetic gases: enflurane, halothane, isoflurane and sevoflurane, and were obtained using the bench reaction cell shown in FIG. 2.

Figure 20:
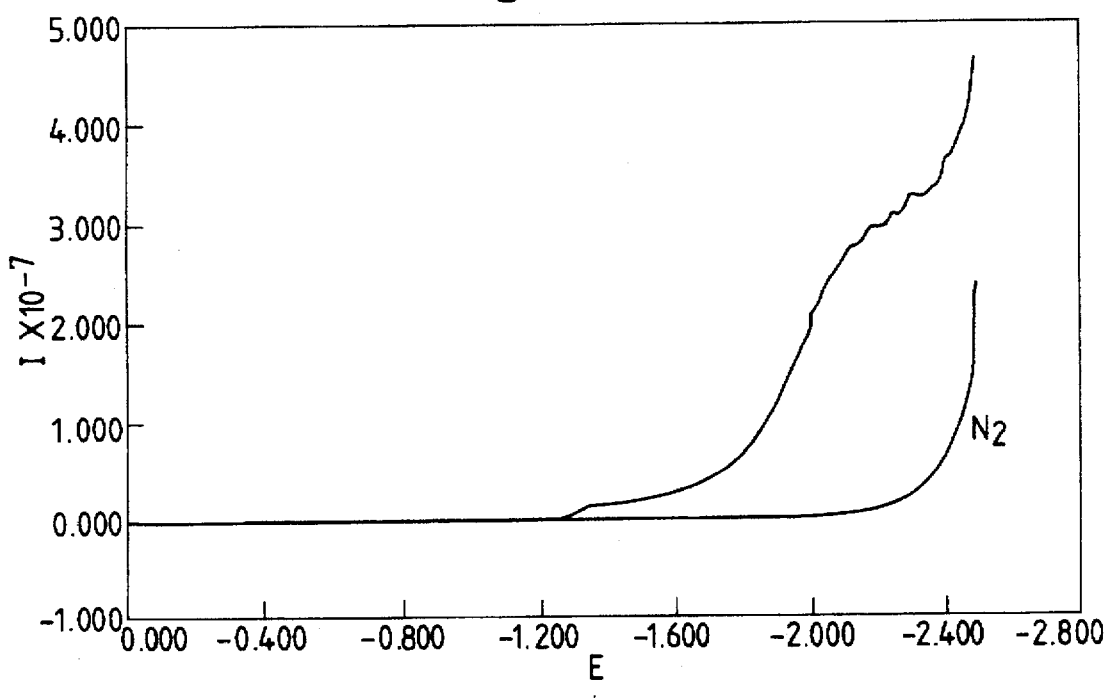

FIG. 20 is a graph of voltage against current for nitrogen gas containing 0.6% v/v of isoflurane, pure $N_2$ gas being also shown for comparison.

Figure 21:
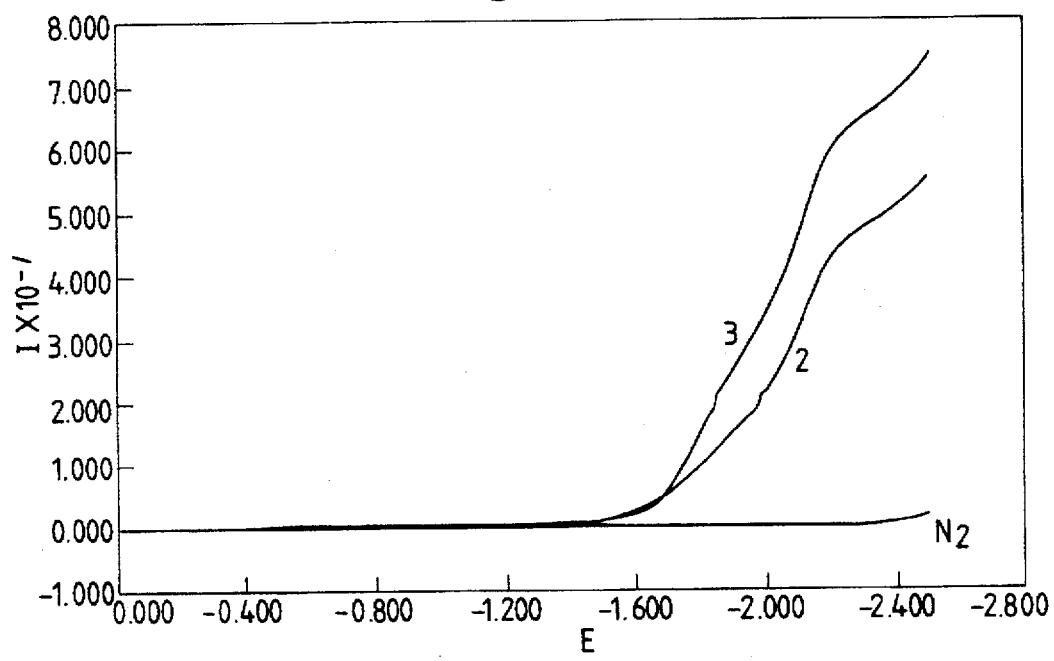
Figure 22:
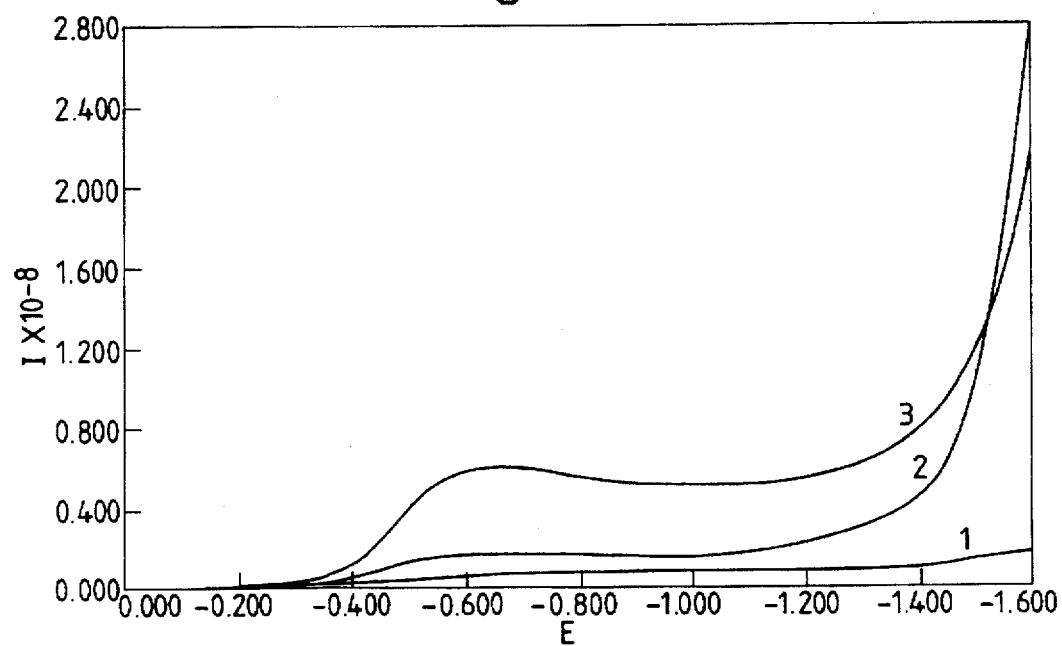

FIGS. 21 and 22 are graphs of voltage against current for 1) $N_2$; 2) 1% v/v of enflurane in nitrogen and 3) 1% v/v of enflurane in a 33% oxygen: 67% nitrogen mixture. The oxygen reduction current is seen to be a minute fraction of the reduction current for enflurane.

FIG. 23 is a graph of voltage against current for each of enflurane, halothane, isoflurane and sevoflurane, all on the same voltage scale, giving a comparison of their respective reduction potentials:

1) ≈1% v/v sevoflurane (after 5 min) in 33% $O_2$/67% $N_2$.

2) ≈1% v/v enflurane (after 5 min) in $N_2$.

3) ≈0.6% v/v halothane (after 6 min) in $N_2$.

4) ≈0.6% v/v isoflurane (after 3 min) in $N_2$.

These results demonstrate that all four of the anaesthetic gases under investigation have been successfully electrochemically reduced (on gold microcathodes in DMSO) using the device and method of the present invention. This is considered to be a surprising finding since previous teachings have indicated that only halothane can be reduced with any ease.

We claim:

1. A method of determining the concentrations of at least one gas in a fluid, which method comprises the steps of:

applying the fluid to one side of a membrane permeable to said at least one gas, the other side of the membrane retaining a solvent for said at least one gas, using a working electrode having a surface area less than 10000 square microns in contact with the solvent and applying a potential which is swept over a range effective to reduce said at least one gas in the solvent, wherein the rate of sweep of potential is sufficient to minimize the interfering effect of any reaction between said at least one gas and a reduction product of any other gas, measuring the current generated at a predetermined potential as an indication of the concentration of said at least one gas, and, where the concentrations of two or more gases are being determined, measuring the current generated at each of one or more further predetermined potentials as an indication of the respective concentrations of the one or more other gases present.

2. A method as claimed in claim 1, wherein the working electrode surface area is less than 100 square microns.

3. A method as claimed in claim 1, wherein said at least one gas comprises oxygen and carbon dioxide.

4. A method as claimed in claim 1, wherein said at least one gas comprises oxygen, carbon dioxide and nitrous oxide.

5. A method as claimed in claim 1, wherein said at least one gas is an anaesthetic gas.

6. A method as claimed in claim 1, wherein said at least one gas comprises an anaesthetic gas together with at least one of oxygen, carbon dioxide and nitrous oxide.

7. A method as claimed in claim 1, wherein the solvent is dimethylsulphoxide.

8. A method as claimed in claim 1, wherein the rate of sweep of potential is from 0.1 to 10 V/s.

9. A method as claimed in claim 1, wherein the working electrode is pre-conditioned by being held at a potential within the sweep range immediately prior to measurement.

* * * * *